(12) United States Patent
Danjo et al.

(10) Patent No.: US 8,329,961 B2
(45) Date of Patent: Dec. 11, 2012

(54) CATALYST FOR PRODUCING ALCOHOL

(75) Inventors: Hiroshi Danjo, Wakayama (JP); Noriaki Fukuoka, Wakayama (JP); Taku Mimura, Wakayama (JP)

(73) Assignee: Kao Corporation, Tokyo (JP)

( * ) Notice: Subject to any disclaimer, the term of this patent is extended or adjusted under 35 U.S.C. 154(b) by 616 days.

(21) Appl. No.: 12/526,518

(22) PCT Filed: Feb. 14, 2008

(86) PCT No.: PCT/JP2008/052905
§ 371 (c)(1),
(2), (4) Date: Aug. 10, 2009

(87) PCT Pub. No.: WO2008/099961
PCT Pub. Date: Aug. 21, 2008

(65) Prior Publication Data
US 2010/0029996 A1    Feb. 4, 2010

(30) Foreign Application Priority Data

Feb. 16, 2007  (JP) ................................ 2007-036525
May 11, 2007  (JP) ................................ 2007-126675
Oct. 3, 2007   (JP) ................................ 2007-259624
Dec. 17, 2007  (JP) ................................ 2007-324714

(51) Int. Cl.
C07C 27/04   (2006.01)
B01J 21/06   (2006.01)
B01J 23/10   (2006.01)
B01J 23/56   (2006.01)
B01J 23/75   (2006.01)

(52) U.S. Cl. ........ 568/885; 502/260; 502/303; 502/304; 502/313; 502/332

(58) Field of Classification Search .................. 568/885; 502/260, 303, 304, 313, 332
See application file for complete search history.

(56) References Cited

U.S. PATENT DOCUMENTS

2005/0272827 A1   12/2005  Lok

FOREIGN PATENT DOCUMENTS

| JP | 48-62708 | 9/1973 |
| JP | 48 62708 | 9/1973 |
| JP | 49-132003 | 12/1974 |
| JP | 49 132003 | 12/1974 |
| JP | 61-5036 | 1/1986 |
| JP | 61 5036 | 1/1986 |
| JP | 61-5086 | 1/1986 |
| JP | 2004 314010 | 11/2004 |
| JP | 2004-314010 | 11/2004 |
| JP | 2005 118676 | 5/2005 |
| JP | 2005-118676 | 5/2005 |
| JP | 2006 513020 | 4/2006 |
| WO | WO 2004-028687 A1 | 4/2004 |

OTHER PUBLICATIONS

Office Action issued on Jul. 20, 2011 in the corresponding Chinese Patent Application No. 200880004991.3 (with English Translation).

*Primary Examiner* — Sikarl Witherspoon
(74) *Attorney, Agent, or Firm* — Oblon, Spivak, McClelland, Maier & Neustadt, L.L.P.

(57) ABSTRACT

The present invention provides a catalyst for producing alcohols from carboxylic acids by hydrogenation, containing Co metal as an essential component and one or more elements selected from Zr, Y, La, Ce, Si, Al, Sc, V and Mo as a first co-catalyst component, and having 20% or more of cubic phase in the crystal phase of the Co metal, the method for producing the catalyst, and the method for producing an alcohol from a carboxylic acid as a raw material by hydrogenation using the catalyst.

17 Claims, 3 Drawing Sheets

CATALYST FOR PRODUCING ALCOHOL

CROSS REFERENCES TO RELATED APPLICATIONS

This application is a 371 of International Patent Application No. PCT/JP08/52905, filed on Feb. 14, 2008, and claims priority to Japanese Patent Application No. 2007-324714, filed on Dec. 17, 2007, Japanese Patent Application No. 2007-259624, filed on Oct. 3, 2007, Japanese Patent Application No. 2007-126675, filed on May 11, 2007, and Japanese Patent Application No. 2007-036525, filed on Feb. 16, 2007.

FIELD OF THE INVENTION

The present invention relates to a catalyst for producing alcohols from carboxylic acids by hydrogenation, a method for producing the catalyst, and a method for producing an alcohol from a carboxylic acid by hydrogenation.

BACKGROUND OF THE INVENTION

As a method for producing alcohols, methods of catalytic hydrogenation of carboxylic acid esters have been commonly known and widely employed in industry. Another approaches for producing alcohols from free carboxylic acids by catalytic hydrogenation have also been attempted. For example, JP-A61-5036 discloses a method for producing an alcohol in the presence of a Co catalyst containing a metal selected from Al, Zr, Mo and Y and a metal selected from Cu, Pt and Pd. JP-A48-62708 discloses a method for producing an alcohol in the presence of a Co catalyst containing composite Fe, Zn, or P.

DISCLOSURE OF THE INVENTION

The present invention (1) provides a catalyst for producing alcohols from carboxylic acids by hydrogenation, containing Co metal as an essential component and one or more elements selected from Zr, Y, La, Ce, Si, Al, Sc, V and Mo as a first co-catalyst component, and having 20% or more of cubic phase in the crystal phase of the Co metal.

The present invention also provides a method for producing the catalyst of the present invention (1) having 20% or more of cubic phase in the crystal phase of the Co metal, including reducing a catalyst precursor containing Co and one or more elements selected from Zr, Y, La, Ce, Si, Al, Sc, V and Mo at a temperature of 300 to 800° C. under hydrogen atmosphere.

The present invention also provides a method for producing an alcohol from a carboxylic acid as a raw material, including hydrogenating a carboxylic acid with the catalyst of the present invention (1).

The present invention also provides use of the catalyst of the present invention (1) for producing an alcohol from a carboxylic acid by hydrogenation.

DETAILED DESCRIPTION OF THE INVENTION

In catalysts that have been studied, only combinations of specific metals are considered for enhancing its activity on an applied reaction and its durability. However, these catalysts do not have an industrially acceptable activity since all of these catalysts have a low activity.

In JP-A61-5036, the catalyst is treated at low temperature and thus has no cubic phase. In JP-A48-62708, the catalyst contains a co-catalyst other than that used in the present invention, or is treated at low temperature when containing the same co-catalyst as that of the present invention, and thus has no cubic phase.

The present invention provides a catalyst used in production of an alcohol from a carboxylic acid by hydrogenation that has industrially acceptable high catalytic activity and a method for producing an alcohol.

The present inventors have found that a catalyst containing Co metal as a main component and a specific co-catalyst component, where the Co metal has a cubic phase in the crystal phase at a specific ratio, has increased catalytic activity, and accomplished the present invention.

The catalyst of the present invention has industrially acceptable high catalytic activity. The catalyst of the present invention allows production of an alcohol from a carboxylic acid as a raw material at high yield, which is very advantageous industrially. The catalyst of the present invention is used in production of an alcohol from a carboxylic or fatty acid by hydrogenation, and has high catalytic activity. The fatty acid may have an ester group.

A preferred aspect (la) of the present invention (1) is a catalyst for producing alcohols from carboxylic acids by hydrogenation, containing Co metal as an essential component and one or more elements selected from Zr, Y, La, Ce, Si, Al, Sc and V as a first co-catalyst component, and having 20% or more of cubic phase in the crystal phase of the Co metal.

A preferred aspect of the present invention is a method for producing the catalyst of the aspect (1a), including reducing a catalyst precursor containing Co and one or more elements selected from Zr, Y, La, Ce, Si, Al, Sc and V at a temperature of 300 to 800° C. under hydrogen atmosphere.

A preferred aspect (2) of the present invention (1) is a catalyst for producing alcohols from carboxylic acids by hydrogenation, containing Co metal as an essential component, one or more elements selected from Zr, Y, La, Ce, Si, Al, Sc and V as a first co-catalyst component and one or more elements selected from Pt and Pd as a second co-catalyst component, and having 20% or more of cubic phase in the crystal phase of the Co metal.

A preferred aspect of the present invention is a method for producing the catalyst of the aspect (2), including reducing a catalyst precursor containing Co, one or more elements selected from Zr, Y, La, Ce, Si, Al, Sc and V and one or more elements selected from Pt and Pd at a temperature of 300 to 800° C. under hydrogen atmosphere.

A preferred aspect (3) of the present invention (1) is a catalyst for producing alcohols from carboxylic acids by hydrogenation, containing Co metal and Mo as essential components, one or more elements selected from Zr, Y, La, Ce, Si, Al, Sc and V as a first co-catalyst component and one or more elements selected from Pt and Pd as a second co-catalyst component, and having 20% or more of cubic phase in the crystal phase of the Co metal.

A preferred aspect is a method for producing the catalyst of the aspect (3), including reducing a catalyst precursor containing Co, Mo, one or more elements selected from Zr, Y, La, Ce, Si, Al, Sc and V and one or more elements selected from Pt and Pd at a temperature of 300 to 800° C. under hydrogen atmosphere.

The present invention (1) including the aspects (2) and (3) will be described below.

[Catalyst for Producing Alcohol]

The catalyst for producing alcohol of the present invention contains Co metal as an essential component and one or more elements selected from Zr, Y, La, Ce, Si, Al, Sc, V and Mo as a first co-catalyst component, and has 20% or more of cubic phase in the crystal phase of the Co metal.

Co metal has two known crystal phases, a cubic phase and a hexagonal phase. The present inventors have found that the presence of the cubic phase largely contributes on catalytic activity. In the catalyst of the present invention, a crystal phase of Co metal is determined according to a measurement with an X-ray crystal diffraction (hereinafter, abbreviated to XRD) measuring apparatus under the following conditions. The cubic phase and the hexagonal phase are distinguished from an XRD peak pattern. A composition of these two phases is determined from detected peak strength.

<Conditions for X-Ray Crystal Diffractometry>

Rigaku RINT2500VPC is used for measurement radiation source; Cu Kα, tube voltage; 40 kV, tube current; 120 mA, scanning rate; 10 deg/min, divergence slit; 1.0 deg, scattering slit; 1.0 deg, receiving slit; 0.3 mm, scanning angle; 5 to 70 deg (reference; POWDER DIFFRACTION FILE)

Co Cubic phase (cubic close-packed structure)

lattice spacing d=2.0467 (first peak/intensity 100), 1.7723 (second peak/relative intensity 40)

lattice constant a=3.5447 Å

Co Hexagonal phase (hexagonal close-packed structure)

lattice spacing d=1.910 (first peak/intensity 100), 2.023 (second peak/relative intensity 60), 2.165 (third peak/relative intensity 20)

lattice constant a, b=2.507 Å, C=4.070 Å.

In the catalyst of the present invention, a percentage of the cubic phase in the crystal phase of the Co metal is not less than 20%, preferably not less than 50%, and more preferably not less than 60%, in accordance with the following formula (1).

<Calculation of a Percentage of the Cubic Phase in the Crystal Phase of the Co Metal>

In the present invention, a percentage of the cubic phase in the crystal phase of the Co metal is determined from a ratio of an intensity of the first peak of the cubic phase (Ic) to an intensity of the first peak of the Hexagonal phase (Ih) by the following formula (1).

In the calculation, since the first peak of the cubic phase is overlapped with the second peak of the Hexagonal phase, the intensity of the first peak of the cubic phase (Ic) is determined by deducting an intensity derived from the second peak of the hexagonal phase (determined as that is 0.6 times larger than the intensity of the first peak of the Hexagonal phase) from an intensity of a peak around d=2.04 at which the first peak of the cubic phase is observed.

That is, an intensity Ic of the first peak of the cubic phase is calculated by the formula, $Ic=I_{2.04}-0.6 \times I_{1.91}$, wherein $I_{1.91}$ is an intensity of a peak around d=1.91, $I_{2.04}$ is an intensity of a peak around d=2.04. A percentage of the cubic phase is calculated by the following formula (1):

$$\text{A percentage of the cubic phase } [\%] = 100 \times Ic/(Ic+Ih) \quad (1)$$

wherein Ih is an intensity of the first peak of the Hexagonal phase, and $Ih=I_{1.91}$.

From the viewpoint of catalytic activity, Co in the catalyst of the present invention is preferably reduced at a rate of not less than 40%, more preferably not less than 70%, and even more preferably not less than 80%. As used herein, the rate of reduction of Co is a value calculated by the method described in Examples.

The first co-catalyst component in the catalyst of the present invention contains one or more elements selected from Zr, Y, La, Ce, Si, Al, Sc, V and Mo. Preferred are Zr, Y, La, Ce and Mo. These elements may be in any chemical state such as metal, oxide and hydroxide. From the viewpoint of catalytic activity, a ratio of the first co-catalyst component to Co is preferably not less than 0.1 mol, and more preferably not less than 1 mol of the first co-catalyst component to 100 mol of Co. The ratio is also preferably not more than 100 mol, and more preferably not more than 25 mol of the first co-catalyst component to 100 mol of Co.

The catalyst of the present invention can further contain the second co-catalyst component selected from Pd and Pt. These components contained in the catalyst can facilitate reduction and decrease a reduction temperature. The catalyst thus can have higher relative surface area to further enhance catalytic activity.

From the viewpoint of catalytic activity, a ratio of the second co-catalyst component to Co is preferably not less than 0.0001 mol, more preferably not less than 0.01 mol, and even more preferably not less than 0.1 mol of the second co-catalyst component to 100 mol of Co. The upper limit of the ratio is not specifically limited, but preferably not more than 10 mol.

The catalyst of the present invention can further contain a carrier. Examples of the carrier include diatom earth, alumina, silica, silica-alumina, magnesia, zirconia, titania, ceria, activated charcoal, and composite oxides thereof. Use of the carrier allows Co and co-catalyst components to be highly dispersed and the catalyst to increase activity. An amount of the carrier in the whole catalyst is preferably not more than 80% by weight, and more preferably not more than 50% by weight.

The catalyst of the present invention can further contain molding components such as a binder and a lubricant.

[Method for Producing a Catalyst]

A method for producing the catalyst of the present invention is not specifically limited, but generally includes steps of preparing a catalyst precursor, drying and baking, and reducing, preferably includes a step of reducing a catalyst precursor containing Co and one or more elements selected from Zr, Y, La, Ce, Si, Al, Sc, V and Mo at a temperature of 300 to 800° C. under hydrogen atmosphere, and more preferably further includes a step of forming an oxide film on the surface of a reduced catalyst to stabilize the catalyst after the step of reducing.

For producing a catalyst precursor, methods of coprecipitation, physical mixing and impregnation are preferably employed.

The method of coprecipitation includes mixing an aqueous mixed solution of respective metal salts of Co and one or more elements selected from Zr, Y, La, Ce, Si, Al, Sc, V and Mo as the first co-catalyst component with a precipitating agent. In this method, the aqueous mixed solution may further contain one or more metal salts of elements selected from Pd and Pt as the second co-catalyst component, and to this may be added a precipitating agent.

The metal salt used can be any salt as long as it is water-soluble. In general, sulfates, nitrates, ammonium salts, acetates and chlorides are used.

The precipitating agent used is an aqueous solution of alkali such as ammonia, urea, ammonium carbonate, sodium hydrogen carbonate, sodium carbonate, sodium hydroxide and potassium hydroxide.

The method of physical mixing contains sufficiently mixing compounds such as oxides, hydroxides, carbonates, phosphates and nitrates of Co, one or more elements selected from Zr, Y, La, Ce, Si, Al, Sc, V and Mo as the first co-catalyst component, and if used, one or more elements selected from Pd and Pt as the second co-catalyst component by physical means.

The method of impregnation includes depositing a metal compound of the co-catalyst component on a Co compound or impregnating the Co compound with the metal compound.

For example, the method includes mixing an aqueous solution of a metal salt that can serve for the co-catalyst component other than Co with the precipitating agent in slurry in which a Co oxide is suspended to produce a precipitate, and washing, drying, and baking the precipitate. Alternatively, the method includes impregnating a Co oxide with an aqueous solution of a metal salt that can serve for the co-catalyst component other than Co to carry the metal salt on the Co oxide.

The catalyst of the present invention can also be supported on known carriers. Examples of the carrier include diatom earth, alumina, silica, silica-alumina, magnesia, zirconia, titania, ceria, activated charcoal, and composite oxides thereof.

When a carrier is used, coprecipitation by mixing a metal salt with a precipitating agent in a slurry in which the carrier is suspended or a simultaneous or sequential impregnation of a carrier with a metal that can serve for the catalyst component is usable.

Among these method for producing a catalyst precursor, coprecipitation and impregnation are preferred.

The catalyst precursor prepared by these methods is preferably dried for 1 to 24 hours at 30 to 120° C. It is preferably then baked generally for 2 to 10 hours at 300 to 800° C. The baking operation produces Co oxide.

Then, the catalyst precursor is reduced. The reducing operation activates the catalyst. Examples of the reducing agent include hydrogen, carbon monoxide and formaldehyde. When a gaseous reducing agent is used, it may be used alone or as a mixture with an inert gas such as nitrogen or water vapor. Among reducing agents, hydrogen is particularly desirably used.

When hydrogen is used, the reducing operation may be performed either in a gas phase system by contacting the catalyst precursor in a dry state with a hydrogen gas or in a liquid phase system by immersing the catalyst precursor in a liquid and passing hydrogen therein. Examples of the liquid that can be used in the liquid phase system include hydrocarbons such as liquid paraffin, aliphatic alcohols, aliphatic esters, and carboxylic acids that are used as raw materials for hydrogenation.

In reducing and activating the catalyst in the gas phase system with hydrogen as the reducing agent, the operation is preferably performed at a temperature of not lower than 300° C., more preferably not lower than 400° C., even more preferably not lower than 420° C., and even more preferably not lower than 450° C. under hydrogen flowing. The hydrogen used may be of 100%, or diluted with an inert gas. To prevent heat generation by rapid reduction, hydrogen is preferably diluted, more preferably diluted to a hydrogen concentrate of 0.5 to 50 vol/vol %, and even more preferably 1 to 10 vol/vol %. The catalyst can be reduced at high rate by such reduction at high temperature to increase a percentage of the cubic phase. In some cases, reduction at high temperature decreases a relative surface area. The reduction temperature is thus preferably not higher than 800° C., and more preferably not higher than 600° C. The reduction is preferably continued until absorption of hydrogen is not detected.

The reduced and activated catalyst, when leaving in the air, can intensely react with oxygen in the air to generate heat. The reduced and activated catalyst is thus preferably provided an oxide film formed on the surface thereof to stabilize. For ease of handling the catalyst, the operation of oxidation and stabilization is preferably performed by placing the catalyst in a flow of an inert gas such as nitrogen containing 0.1 to 5% by volume of oxygen for 1 to 24 hours at 0 to 200° C., preferably 20 to 100° C., more preferably 20 to 50° C. to form an oxide film on the surface of the catalyst and thereby stabilize it.

[Method for Producing Alcohol]

The method for producing an alcohol of the present invention is a method of hydrogenation of a carboxylic acid as a raw material with the catalyst of the present invention.

The carboxylic acid used in the present invention may be either a monocarboxylic or polycarboxylic acid. Examples of the monocarboxylic acid used include aliphatic, aromatic, aroma-aliphatic and alicyclic carboxylic acids. Examples of the polycarboxylic acid used include aliphatic and aromatic dicarboxylic acids. Examples of the carboxylic acid include acetic acid, propionic acid, butyric acid, isobutyric acid, valeric acid, caproic acid, caprylic acid, capric acid, lauric acid, myristic acid, palmitic acid, stearic acid, oleic acid, isostearic acid, benzoic acid, oxalic acid, tartaric acid, maleic acid, succinic acid, glutaric acid, adipic acid, azelaic acid and cyclohexanecarboxylic acid. These carboxylic acids may be of either free carboxylic acid or acid anhydride. These carboxylic acids may also have an additional functional group other than the carboxyl group such as an amino group, an alkoxy group, a halogen group such as a chloro group, a phosphonic acid group, and a sulfonic acid group.

Organocarboxylic acids such as methyl esters and oil-and-fat contained in other compounds may also be used as raw materials.

The method for producing an alcohol of the present invention can be performed in either of a suspension bed or a fixed bed reaction system. For example, in the suspension bed reaction system, a powder catalyst is used under reaction conditions as follows. A reaction temperature is preferably 150 to 300° C. A reaction pressure is preferably 1 to 30 MPa, and more preferably 5 to 30 MPa. An amount of catalyst used is preferably 0.5 to 20% by weight, and more preferably 1 to 10% by weight of the carboxylic acid raw material. The amount of catalyst used can be determined without limitation within the range that can provide a practical reaction rate according to the reaction temperature and the reaction pressure.

In the fixed bed reaction system, a catalyst formed according to an intended use is used. A reaction temperature is preferably 150 to 300° C., and more preferably 180 to 250° C. A reaction pressure is preferably 1 to 30 MPa, and more preferably 5 to 30 MPa. In this system, a liquid space velocity (LHSV) is arbitrarily determined according to reaction conditions, but desirably within the range of 0.2 to 5 [1/hr] considering with productivity or reactivity.

The reaction may be performed in a solvent, but desirably without a solvent considering with productivity. The solvent selected is those not affecting the reaction, including alcohols, ethers such as dioxane, and hydrocarbons.

In the aspect (2), a reduction rate of Co in the catalyst is preferably not less than 40%, more preferably not less than 70%, and even more preferably not less than 80%, from the viewpoint of catalytic activity. The reduction rate of Co is calculated from a measured weight loss to a theoretical weight loss from Co oxide ($Co_3O_4$) to Co metal in the catalyst that is considered as 100.

In the aspect (2), the first co-catalyst component in the catalyst contains one or more elements selected from Zr, Y, La, Ce, Si, Al, Sc and V. Among these elements, preferred are Zr, Y, La and Ce. These elements may be in any chemical form such as metal, oxide, and hydroxide. From the viewpoint of catalytic activity, a ratio of the first co-catalyst component to Co is preferably not less than 0.1 mol, more preferably not less than 1 mol to 100 mol of Co, and is preferably not more than 100 mol and more preferably not more than 25 mol to 100 mol of Co.

In the aspect (2), the second co-catalyst component contains one or more elements selected from Pt and Pd, preferably Pd. These elements may be in any chemical form such as metal, oxide, and hydroxide. The presence of the second co-catalyst in the catalyst will facilitate reduction and decrease a reduction temperature, resulting in higher specific surface area and more increased activity.

In the aspect (2), from the viewpoint of catalytic activity, a ratio of the second co-catalyst component to Co is preferably not less than 0.0001 mol, more preferably not less than 0.01 mol, and even more preferably 0.05 mol to 100 mol of Co. The upper limit thereof is not specifically limited, but preferably not more than 10 mol.

In the aspect (2), a method for producing the catalyst of the present invention is not specifically limited, but generally includes each steps of preparing a catalyst precursor, drying and baking, and reducing. The method preferably includes a step of reducing a catalyst precursor containing Co, one or more elements selected from Zr, Y, La, Ce, Si, Al, Sc and V and one or more elements selected from Pt and Pd at 300 to 800° C. under hydrogen atmosphere, and more preferably further includes a step of forming an oxide film on the surface of the reduced catalyst to stabilize after the step of reduction.

In the aspect (2), a method of coprecipitation includes mixing an aqueous mixed solution of respective metal salts of Co, one or more elements selected from Zr, Y, La, Ce, Si, Al, Sc and V as the first co-catalyst component and one or more elements selected from Pt and Pd as the second co-catalyst component with an precipitating agent.

In the aspect (2), a method of physical mixing contains sufficiently mixing compounds such as oxides, hydroxides, carbonates, phosphates and nitrates of Co, one or more elements selected from Zr, Y, La, Ce, Si, Al, Sc and V as the first co-catalyst component, and one or more elements selected from Pd and Pt as the second co-catalyst component by physical means.

In the aspect (3), the catalyst containing Co metal, Mo and a specific co-catalyst component in which the Co metal as the main component of the catalyst has a cubic phase at a specific percentage in the crystal phase has increased catalytic activity and durability.

In the aspect (3), the catalyst contains Co metal and Mo as essential components, one or more elements selected from Zr, Y, La, Ce, Si, Al, Sc and V as the first co-catalyst component and one or more elements selected from Pt and Pd as the second co-catalyst component, and has 20% or more of cubic phase in the crystal phase of the Co metal.

In the aspect (3), Co metal has two known crystal phases, a cubic phase and a hexagonal phase. The present inventors have found that the presence of the cubic phase largely contributes on catalytic activity. In the catalyst of the present invention, a crystal phase of a Co metal is determined according to a measurement with an X-ray crystal diffraction (hereinafter, abbreviated to XRD) measuring apparatus under the following conditions. The cubic phase and the hexagonal phase are distinguished from an XRD peak pattern. A composition of these two phases is determined from detected peak strength.

In the aspect (3), from the viewpoint of catalytic activity, a reduction rate of Co in the catalyst is preferably not less than 40%, more preferably not less than 70%, and even more preferably not less than 80%. The reduction rate of Co is calculated from a measured weight loss to a theoretical weight loss from Co oxide ($Co_3O_4$) to Co metal in the catalyst that is considered as 100.

In the aspect (3), Mo in the catalyst may be in any chemical form such as metal, oxide, and hydroxide. From the viewpoint of catalytic activity, a ratio of Mo to Co is preferably not less than 0.05 mol, and more preferably not less than 0.5 mol to 100 mol of Co, and is preferably not more than 100 mol, and more preferably not more than 25 mol to 100 mol of Co.

In the aspect (3), the first co-catalyst component in the catalyst contains one or more elements selected from Zr, Y, La, Ce, Si, Al, Sc and V. Among these elements, preferred are Zr, Y, La and Ce. These elements may be in any chemical form such as metal, oxide, and hydroxide. From the viewpoint of catalytic activity, a ratio of the first co-catalyst component to Co is preferably not less than 0.1 mol, more preferably not less than 1 mol to 100 mol of Co, and is preferably not more than 100 mol and more preferably not more than 25 mol to 100 mol of Co.

In the aspect (3), the second co-catalyst component in the catalyst contains one or more elements selected from Pt and Pd, preferably Pd. These elements may be in any chemical form such as metal, oxide, and hydroxide. The presence of the second co-catalyst in the catalyst will facilitate reduction and decrease a reduction temperature, resulting in higher specific surface area and more increased activity.

In the aspect (3), from the viewpoint of catalytic activity, a ratio of the second co-catalyst component to Co is preferably not less than 0.0001 mol, more preferably not less than 0.01 mol, and even more preferably not less than 0.05 mol to 100 mol of Co. The upper limit thereof is not specifically limited, but preferably not more than 10 mol.

In the aspect (3), the catalyst can further contain a carrier. Examples of the carrier include diatom earth, alumina, silica, silica-alumina, magnesia, zirconia, titania, ceria, activated charcoal, and composite oxides thereof. Use of the carrier allows Co, Mo and co-catalyst components to be highly dispersed and the catalyst to increase activity. An amount of the carrier in the whole catalyst is preferably not more than 80% by weight, and more preferably not more than 50% by weight.

In the aspect (3), a method for producing the catalyst of the present invention is not specifically limited, but generally includes steps of preparing a catalyst precursor, drying and baking, and reducing. For example, a catalyst precursor containing Co, Mo, one or more elements selected from Zr, Y, La, Ce, Si, Al, Sc and V and one or more elements selected from Pt and Pd is reduced at high temperature (preferably 300 to 800° C.) under hydrogen atmosphere to produce a catalyst having a desired cubic phase. It should be noted that the method preferably further includes a step of forming an oxide film on the surface of the reduced catalyst to stabilize it after the step of reduction.

In the aspect (3), a method of impregnation includes adding an aqueous solution of an Mo compound to a compound containing Co, one or more elements selected from Zr, Y, La, Ce, Si, Al, Sc and V as the first co-catalyst component and one or more elements selected from Pt and Pd as the second co-catalyst components for impregnation. The compound containing Co and co-catalyst components used can be prepared by mixing an aqueous mixed solution of respective metal salts of Co and co-catalyst components with an precipitating agent to produce a precipitate, washing with water and drying the precipitate, and further baking and forming.

In the aspect (3), any metal salts of Co and co-catalyst components can be used as long as these metal salts are water-soluble. Examples of the metal salt include sulfates, nitrates, ammonium complex salts, acetates and chlorides. Examples of the precipitating agent used include an aqueous solution of alkali such as ammonia, urea, ammonium carbonate, sodium hydrogen carbonate, sodium carbonate, sodium hydroxide, and potassium hydroxide.

In the aspect (3), examples of the Mo compound include acids such as p-molybdic acid, m-molybdic acid, pyromolybdic acid, molybdenum-containing heteropoly acid and phosphomolybdic acid; salts such as sodium molybdate dihydrate ($Na_2MoO_4 \cdot 2H_2O$) and hexaammonium heptamolybdate tetrahydrate $[(NH_4)_6Mo_7O_{24} \cdot 4H_2O]$; oxides such as molybdenum trioxide ($MoO_3$); and halides such as molybdenum chloride ($MoOCl_4$, $MoO_2Cl_2$).

In the aspect (3), a method of coprecipitation includes mixing an aqueous mixed solution of respective metal salts of Co, Mo, one or more elements selected from Zr, Y, La, Ce, Si, Al, Sc and V as the first co-catalyst component and one or more elements selected from Pt and Pd as the second co-catalyst component with an precipitating agent. As the metal salt and the precipitating agent, those described above can be used.

In the aspect (3), a method of physical mixing contains sufficiently mixing compounds such as oxides, hydroxides, carbonates, phosphates and nitrates of Co, one or more elements selected from Zr, Y, La, Ce, Si, Al, Sc and V as the first co-catalyst component, and one or more elements selected from Pd and Pt as the second co-catalyst component by physical means, and drying the mixture, or drying and baking the mixture, then sufficiently mixing the mixture with the acid, the salt thereof, the oxide, or the hydroxide of Mo described above by physical means, which step may be simultaneously performed with forming with a carrier.

In the aspect (3), the catalyst can be supported on a carrier. Examples of the carrier include diatom earth, alumina, silica, silica-alumina, magnesia, zirconia, titania, ceria, activated charcoal, and composite oxides thereof.

In the aspect (3), a method of producing a catalyst supported on the carrier include methods of coprecipitation by mixing metals salts with a precipitating agent in slurry containing the carrier suspended therein and of impregnation of the carrier with metals serving for catalyst components simultaneously or sequentially.

In the aspect (3), among methods for preparing a catalyst precursor, preferred are impregnation and coprecipitation.

In the aspect (3), any method can be used to support catalyst components on a carrier or mix the components with the carrier without specific limitation. For example, the following methods can be used. A method includes adding a precipitating agent to an aqueous solution of metal salts serving for catalyst components other than a carrier component in the presence of the carrier component to produce a precipitate, which precipitate is washed with water, dried, and baked. Another method includes impregnating a carrier component with an aqueous solution of metal salts serving for catalyst components other than the carrier component, drying, and baking. Still another method includes mixing a carrier component with compounds (e.g., oxides, hydroxides, carbonates) of metal elements constructing a catalyst component uniformly and baking.

BRIEF DESCRIPTION OF THE DRAWINGS

FIG. 2-1 shows a peak pattern obtained by XRD analysis of a catalyst prepared in Example 2-1

FIG. 3-1 shows a peak pattern obtained by XRD analysis of a catalyst prepared in Example 3-1.

EXAMPLES

The following Examples demonstrate the present invention. Examples are intended to illustrate the present invention and not to limit the present invention.

A reduction rate of Co described in Examples and Comparative Examples was calculated as follows.
<Method of Calculating a Reduction Rate of Co>

A reduction rate of Co was determined as follows from a weight loss of the catalyst before and after activated and stabilized by temperature programmed hydrogen reduction for activation, which was considered as reduction of cobalt oxide to metal cobalt, and a cobalt content in the catalyst separately determined by composition analysis. In all the reduced samples, elemental cobalt was present as Co metal or cobalt oxide (CoO).

In 20 g (a) of baked catalyst in which an atom ratio of Co/Zr=100/2.2, an amount of $Co_3O_4$ (molecular weight: 240.8) in the baked catalyst is 19.4 g (b). In activation and stabilization of the baked catalyst, when $Co_3O_4$ reduced to CoO (molecular weight: 76.9) and then to Co metal, theoretical amounts of CoO and Co are 18.6 g (c) and 14.2 g (d), respectively. If a weight of the catalyst after activation and stabilization is 15.3 g (e), an apparent weight loss is a−e=4.7 g (f). Since only elemental cobalt is reduced, a real weight derived from elemental Co is b−f=14.7 g (g) Accordingly, the reduction rate was calculated as follows.

$$\text{reduction rate of Co } (\%) = 100 \times (c-g)/(c-d) = 89\%$$

Example 1-1

(1) Preparation of a Catalyst Precursor

An aqueous solution of cobalt nitrate and zirconium oxynitrate mixed at 100:5 atom ratio of cobalt to zirconium and an aqueous ammonium carbonate solution were mixed and stirred at room temperature to produce a precipitate. The precipitate was sufficiently washed with water, dried at 110° C., and baked for 4 hours at 600° C. to give a Co—Zr oxide.

In the resultant baked catalyst, an atom ratio was Co/Zr=100/2.2.

(2) Activation of a Catalyst

Figure 1:
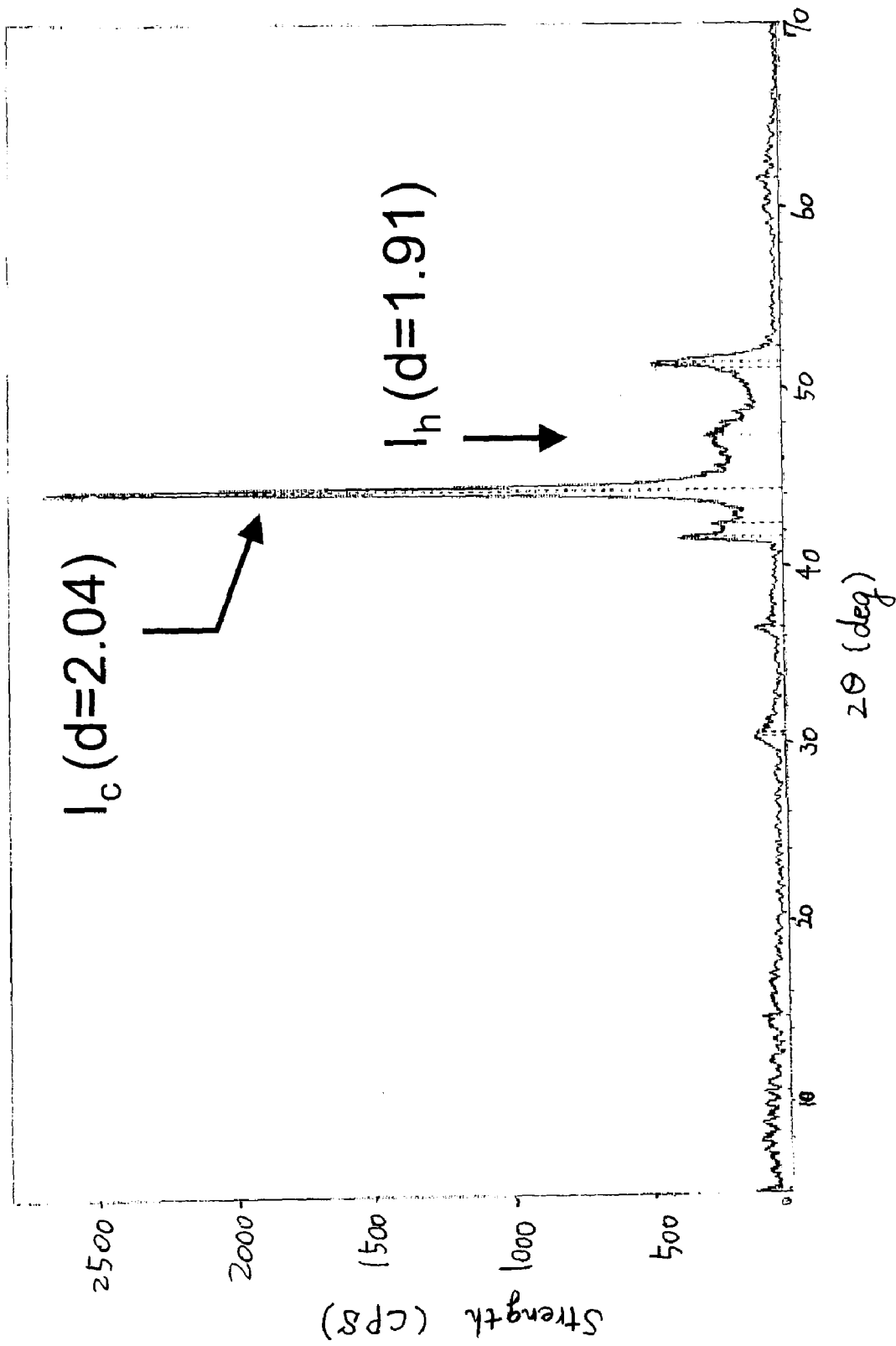
FIG. 1-1 shows a peak pattern obtained by XRD analysis of a catalyst prepared in Example 1-1.

The baked catalyst (oxide) placed on a sintering dish was set in an electric furnace the inside thereof can be made to a reducing atmosphere. The furnace was flowed with 4% [v/v] of hydrogen in nitrogen and raised to 500° C. The catalyst was subjected to a reduction treatment until hydrogen absorption was not detected. A reduction treatment time was 5 hours. The inside of the system was replaced with nitrogen and cooled to room temperature. Then, the furnace was flowed with the air diluted with nitrogen (oxygen concentration: 1% v/v) to oxidize and stabilize the surface of the reduced catalyst. The catalyst was subjected to the oxidation and stabilization treatment until oxygen absorption was not detected. The resultant catalyst was measured to calculate a reduction rate of Co, and subjected to XRD analysis to give a peak pattern shown in FIG. 1. From the peak pattern, a percentage of the cubic phase in the crystal phase of Co metal was determined. Results are shown in table 1-1.

(3) Production of Alcohol 3.75 g (weight based on oxide) of the resultant catalyst and 150 g of lauric acid were charged in a 500 ml autoclave. The inside of the autoclave was substituted with hydrogen. The reaction was conducted for 2 hours under conditions of 230° C./24.5 MPa/900 rpm/hydrogen 5 L/min flow. After the end of reaction, the autoclave was cooled and the pressure was released. The reaction mixture was filtered to collect a product. A composition of the product was determined by gas chromatography (GC) analysis as follows. A composition of produced alcohol and residual fatty acid after the reaction is shown in Table 1-1.

<Method of GC Analysis>

One drop of a reaction product was placed in a 10 ml sample vial. To this was added a trimethylsilylating (TMS) agent (TMSI-H/GL Sciences Inc.) and treated for about 5 minutes (warming to 40° C.). The mixture was diluted with 1.5 ml of hexane, filtered through a membrane filter 0.2μ, and analyzed by GC.

GC measurement conditions: HP-6890
   capillary column: Ultra-AlloyUA*-1 (HT) 15 m, membrane thickness 0.15 μm
   temperature 60° C. (2 minutes)→10° C./min→350° C.
   split ratio 15, Inj temperature 300° C., Det temperature 350° C.

Example 1-2

(1) Preparation of a Catalyst Precursor

A Co—Zr oxide was prepared by the same method as (1) in Example 1-1.

(2) Activation of a Catalyst

The catalyst was reduced, oxidized and activated by the same method as (2) in Example 1-1, except that a catalyst reducing temperature was 400° C. A reduction rate of Co of the resultant catalyst and a percentage of a cubic phase in the crystal phase of Co metal are shown in Table 1-1.

(3) Production of Alcohol

An alcohol was produced by the same method as (3) in Example 1-1 using the resultant catalyst. A composition of produced alcohol and residual fatty acid after the reaction is shown in Table 1-1.

Example 1-3

(1) Preparation of a Catalyst Precursor

A Co—Zr oxide was prepared by the same method as (1) in Example 1-1.

(2) Activation of a Catalyst

The catalyst was reduced, oxidized and activated by the same method as (2) in Example 1-1, except that a catalyst reducing temperature was 320° C. A reduction rate of Co of the resultant catalyst and a percentage of a cubic phase in the crystal phase of Co metal are shown in Table 1-1.

(3) Production of Alcohol

An alcohol was produced by the same method as (3) in Example 1-1 using the resultant catalyst. A composition of produced alcohol and residual fatty acid after the reaction is shown in Table 1-1.

Comparative Example 1-1

(1) Preparation of a Catalyst Precursor

A Co—Zr oxide was prepared by the same method as (1) in Example 1-1.

(2) Activation of a Catalyst

The baked catalyst (oxide) and lauryl alcohol were charged in a 500 ml autoclave. The inside of the autoclave was substituted with hydrogen and raised to 5 MPa. The mixture was treated for 30 minutes at 250° C. The autoclave was cooled and the pressure was released. The reaction mixture was filtered to give a catalyst cake. For the catalyst cake, a percentage of a cubic phase in the crystal phase of Co metal is shown in Table 1-1.

(3) Production of Alcohol

An alcohol was produced by the same method as (3) in Example 1-1 using the resultant catalyst cake (7.5 g as dry oxide). A composition of produced alcohol and residual fatty acid after the reaction is shown in Table 1-1.

Example 1-4

(1) Preparation of a Catalyst Precursor

A Co—Y oxide was prepared by the same method as (1) in Example 1-1, except that an aqueous solution of cobalt nitrate and yttrium nitrate (n-hydrate) mixed at 100:5 atom ratio of cobalt to yttrium was used. In the resultant baked catalyst, an atom ratio was Co/Y=100/3.7.

(2) Activation of a Catalyst

The resultant baked catalyst (oxide) was reduced, oxidized and activated by the same method as (2) in Example 1-1. A reduction rate of Co of the resultant catalyst and a percentage of a cubic phase in the crystal phase of Co metal are shown in Table 1-1.

(3) Production of Alcohol

An alcohol was produced by the same method as (3) in Example 1-1 using the resultant catalyst. A composition of produced alcohol and residual fatty acid after the reaction is shown in Table 1-1.

Comparative Example 1-2

(1) Preparation of a Catalyst Precursor

A Co—Y oxide was prepared by the same method as (1) in Example 1-4.

(2) Activation of a Catalyst

The catalyst was reduced by the same method as (2) in Comparative Example 1-1. A percentage of a cubic phase in the crystal phase of Co metal in the resultant catalyst is shown in Table 1-1.

(3) Production of Alcohol

An alcohol was produced by the same method as (3) in Example 1-1 using the resultant catalyst cake (3.75 g as dry oxide). A composition of produced alcohol and residual fatty acid after the reaction is shown in Table 1-1.

Example 1-5

(1) Preparation of a Catalyst Precursor

A Co—Al oxide was prepared by the same method as (1) in Example 1-1, except that an aqueous solution of cobalt nitrate and aluminium nitrate (enneahydrate) mixed at 100:5 atom ratio of cobalt to aluminium was used. In the resultant baked catalyst, an atom ratio was Co/Al=100/9.6.

(2) Activation of a Catalyst

The resultant baked catalyst (oxide) was reduced, oxidized and activated by the same method as (2) in Example 1-1. A reduction rate of Co of the resultant catalyst and a percentage of a cubic phase in the crystal phase of Co metal are shown in Table 1-1.

(3) Production of Alcohol

An alcohol was produced by the same method as (3) in Example 1-1 using the resultant catalyst. A composition of produced alcohol and residual fatty acid after the reaction is shown in Table 1-1.

Example 1-6

(1) Preparation of a Catalyst Precursor

A Co—Si oxide was prepared by the same method as (1) in Example 1-1, except that an aqueous solution of cobalt nitrate and water glass mixed at 100:5 atom ratio of cobalt to silica was used. In the resultant baked catalyst, an atom ratio was Co/Si=100/4.9.

(2) Activation of a Catalyst

The resultant baked catalyst (oxide) was reduced, oxidized and activated by the same method as (2) in Example 1-1. A reduction rate of Co of the resultant catalyst and a percentage of a cubic phase in the crystal phase of Co metal are shown in Table 1-1.

(3) Production of Alcohol

An alcohol was produced by the same method as (3) in Example 1-1 using the resultant catalyst. A composition of produced alcohol and residual fatty acid after the reaction is shown in Table 1-1.

Example 1-7

(1) Preparation of a Catalyst Precursor

A Co—La oxide was prepared by the same method as (1) in Example 1-1, except that an aqueous solution of cobalt nitrate and lanthanum nitrate (hexahydrate) mixed at 100:5 atom ratio of cobalt to lanthanum was used. In the resultant baked catalyst, an atom ratio was Co/La=100/6.0.

(2) Activation of a Catalyst

The resultant baked catalyst (oxide) was reduced, oxidized and activated by the same method as (2) in Example 1-1. A reduction rate of Co of the resultant catalyst and a percentage of a cubic phase in the crystal phase of Co metal are shown in Table 1-1.

(3) Production of Alcohol

An alcohol was produced by the same method as (3) in Example 1-1 using the resultant catalyst. A composition of produced alcohol and residual fatty acid after the reaction is shown in Table 1-1.

Example 1-8

(1) Preparation of a Catalyst Precursor

A Co—Ce oxide was prepared by the same method as (1) in Example 1-1, except that an aqueous solution of cobalt nitrate and cerium nitrate (hexahydrate) mixed at 100:5 atom ratio of cobalt to cerium was used. In the resultant baked catalyst, an atom ratio was Co/Ce=100/5.1.

(2) Activation of a Catalyst

The resultant baked catalyst (oxide) was reduced, oxidized and activated by the same method as (2) in Example 1-1. A reduction rate of Co of the resultant catalyst and a percentage of a cubic phase in the crystal phase of Co metal are shown in Table 1-1.

(3) Production of Alcohol

An alcohol was produced by the same method as (3) in Example 1-1 using the resultant catalyst. A composition of produced alcohol and residual fatty acid after the reaction is shown in Table 1-1.

Comparative Example 1-3

(1) Preparation of a Catalyst Precursor

A Co oxide was prepared by the same method as (1) in Example 1-1, except that an aqueous solution of cobalt nitrate only was used.

(2) Activation of a Catalyst

The resultant baked catalyst (oxide) was reduced, oxidized and activated by the same method as (2) in Example 1-1. A reduction rate of Co of the resultant catalyst and a composition of the crystal phase of Co metal are shown in Table 1-1.

(3) Production of Alcohol

An alcohol was produced by the same method as (3) in Example 1-1 using the resultant catalyst. A composition of produced alcohol and residual fatty acid after the reaction is shown in Table 1-1.

Comparative Example 1-4

(1) Preparation of a Catalyst Precursor

A Co—Fe oxide was prepared by the same method as (1) in Example 1-1, except that an aqueous solution of cobalt nitrate and iron(III) nitrate (enneahydrate) mixed at 100:5 atom ratio of cobalt to iron was used. In the resultant baked catalyst, an atom ratio was Co/Fe=100/5.0.

(2) Activation of a Catalyst

The resultant baked catalyst (oxide) was reduced, oxidized and activated by the same method as (2) in Example 1-1. A reduction rate of Co of the resultant catalyst and a percentage of a cubic phase in the crystal phase of Co metal are shown in Table 1-1.

(3) Production of Alcohol

An alcohol was produced by the same method as (3) in Example 1-1 using the resultant catalyst. A composition of produced alcohol and residual fatty acid after the reaction is shown in Table 1-1.

Example 1-9

(1) Preparation of a Catalyst Precursor

A Co—Mo oxide was prepared by the same method as (1) in Example 1-1, except that an aqueous solution of cobalt nitrate and ammonium molybdate (tetrahydrate) mixed at 100:35 atom ratio of cobalt to molybdenum was used. In the resultant baked catalyst, an atom ratio was Co/Mo=100/5.9.

(2) Activation of a Catalyst

The resultant baked catalyst (oxide) was reduced, oxidized and activated by the same method as (2) in Example 1-1. A reduction rate of Co of the resultant catalyst and a percentage of a cubic phase in the crystal phase of Co metal are shown in Table 1-1.

(3) Production of Alcohol

An alcohol was produced by the same method as (3) in Example 1-1 using the resultant catalyst. A composition of produced alcohol and residual fatty acid after the reaction is shown in Table 1-1.

Example 1-10

(1) Preparation of a Catalyst Precursor

A Co—Mo oxide was prepared by the same method as (1) in Example 1-1, except that an aqueous solution of cobalt nitrate and ammonium molybdate (tetrahydrate) mixed at 100:5 atom ratio of cobalt to molybdenum was used. In the resultant baked catalyst, an atom ratio was Co/Mo=100/0.7.

(2) Activation of a Catalyst

The resultant baked catalyst (oxide) was reduced, oxidized and activated by the same method as (2) in Example 1-1. A reduction rate of Co of the resultant catalyst and a percentage of a cubic phase in the crystal phase of Co metal are shown in Table 1-1.

(3) Production of Alcohol

An alcohol was produced by the same method as (3) in Example 1-1 using the resultant catalyst. A composition of produced alcohol and residual fatty acid after the reaction is shown in Table 1-1.

Comparative Example 1-5

(1) Preparation of a Catalyst Precursor

A Co—Mo oxide was prepared by the same method as (1) in Example 1-9.

(2) Activation of a Catalyst

The catalyst was reduced, oxidized and activated by the same method as (2) in Example 1-1, except that a catalyst reducing temperature was 350° C. A reduction rate of Co of the resultant catalyst and a percentage of a cubic phase in the crystal phase of Co metal are shown in Table 1-1.

This is the same catalyst as described in JP-A48-62708.

(3) Production of Alcohol

An alcohol was produced by the same method as (3) in Example 1-1 using the resultant catalyst. A composition of produced alcohol and residual fatty acid after the reaction is shown in Table 1-1.

TABLE 1-1

| | Kind of catalyst | Reduction rate of Co (%) | percentage of cubic phase in the crystal phase of Co metal (%) | Amount of used catalyst (%)*1 | Composition of reaction product | |
|---|---|---|---|---|---|---|
| | | | | | Produced alcohol (%) | Residual fatty acid (%) |
| Example 1-1 | Co—Zr | 89 | 90 | 2.5 | 72.5 | 0.00 |
| Example 1-2 | Co—Zr | 76 | 79 | 2.5 | 70.3 | 0.00 |
| Example 1-3 | Co—Zr | 43 | 70 | 2.5 | 48.2 | 0.03 |
| Comparative example 1-1 | Co—Zr | 0*2 | 0*2 | 5.0 | 34.7 | 1.75 |
| Example 1-4 | Co—Y | 53 | 100 | 2.5 | 61.7 | 0.02 |
| Comparative example 1-2 | Co—Y | 0*2 | 0*2 | 2.5 | 3.25 | 44.3 |
| Example 1-5 | Co—Al | 76 | 100 | 2.5 | 68.4 | 0.00 |
| Example 1-6 | Co—Si | 93 | 91 | 2.5 | 36.0 | 0.00 |
| Example 1-7 | Co—La | 90 | 100 | 2.5 | 62.6 | 0.02 |
| Example 1-8 | Co—Ce | 85 | 74 | 2.5 | 57.6 | 0.03 |
| Comparative example 1-3 | Co | 100 | 97 | 2.5 | 1.99 | 55.4 |
| Comparative example 1-4 | Co—Fe | 100 | 100 | 2.5 | 0.02 | 98.3 |
| Example 1-9 | Co—Mo | 84 | 100 | 2.5 | 40.5 | 0.04 |
| Example 1-10 | Co—Mo | 81 | 87 | 2.5 | 44.4 | 0.03 |
| Comparative example 1-5 | Co—Mo | 23 | 0*2 | 2.5 | 2.17 | 56.3 |

*1 weight of catalyst converted to oxide, relative to fatty acid raw material
*2 In XRD analysis of activated catalyst, a crystal phase of Co metal was not detected and showed as "0%" for convenience of indication.

The aspect (2) will be described with reference to Examples below.

Example 2-1

(1) Preparation of a Catalyst Precursor

An aqueous solution of cobalt nitrate, yttrium nitrate (n-hydrate), and palladium nitrate mixed at 100:5:0.08 atom ratio of cobalt to yttrium to palladium and an aqueous ammonium carbonate solution were mixed and stirred at room temperature to produce a precipitate. The precipitate was sufficiently washed with water, dried at 110° C., and baked for 4 hours at 600° C. to give a Co—Y—Pd oxide. In the resultant baked catalyst, an atom ratio was Co/Y/Pd=100/4.2/0.08.

(2) Activation of a Catalyst

Figures 1, 2:
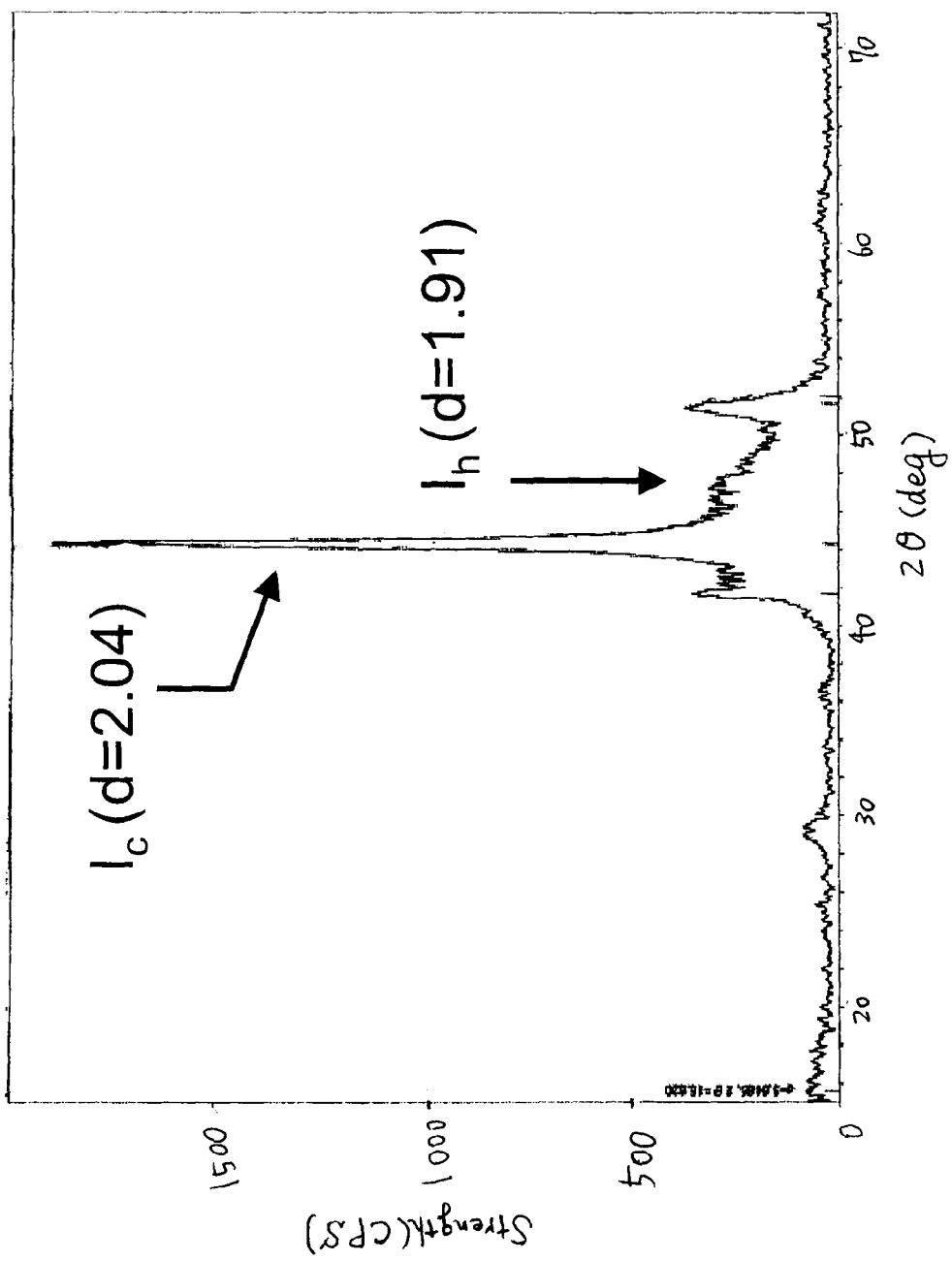

The baked catalyst (oxide) placed on a sintering dish was set in an electric furnace the inside thereof can be made to a reducing atmosphere. The furnace was flowed with 4% [v/v] of hydrogen diluted with nitrogen and raised to 500° C. The catalyst was subjected to a reduction treatment until hydrogen absorption was not detected. A reduction treatment time was 5 hours. The inside of the system was replaced with nitrogen and cooled to room temperature. Then, the furnace was flowed with the air diluted with nitrogen (oxygen concentration: 1% v/v) to oxidize and stabilize the surface of a reduced catalyst. The catalyst was subjected to the oxidation and stabilization treatment until oxygen absorption was not detected. A reduction rate of Co of the resultant catalyst was calculated as a found weight loss in relation to a theoretical weight loss of 100 of Co oxide ($Co_3O_4$) to Co metal in the catalyst. The catalyst was subjected to XRD analysis to give a peak pattern shown in FIG. 2-1. From the peak pattern, a percentage of a cubic phase in the crystal phase of Co metal was determined. Results are shown in table 2-1.

(3) Production of Alcohol 3.75 g (weight based on oxide) of the resultant catalyst and 150 g of lauric acid were charged in a 500 ml autoclave. The inside of the autoclave was substituted with hydrogen. The reaction was conducted for 40 minutes under conditions of 230° C./24.5 MPa/900 rpm/hydrogen 5 L/min flow. After the end of reaction, the autoclave was cooled and the pressure was released. The reaction mixture was filtered to collect a product. A composition of the product was determined by gas chromatography (GC) analysis as follows. A composition of produced alcohol and residual fatty acid after the reaction is shown in Table 2-1.

Example 2-2

(1) Preparation of a Catalyst Precursor

An aqueous solution of cobalt nitrate and zirconium oxynitrate mixed at 100:5 atom ratio of cobalt to zirconium and an aqueous ammonium carbonate solution were mixed and stirred at room temperature to produce a precipitate. The precipitate was sufficiently washed with water, dried at 110° C., and baked for 4 hours at 600° C. to give a Co—Zr oxide. In the resultant baked catalyst, an atom ratio was Co/Zr=100/2.2.

To the resultant Co—Zr oxide was added an aqueous solution of palladium nitrate prepared such that Pd was 0.1% by weight of the oxide, and sufficiently mixed to impregnate with Pd. The oxide was then dried at 110° C. to give a Co—Zr oxide supported on palladium.

(2) Activation of a Catalyst

The catalyst was reduced, oxidized and stabilized by the same method as (2) in Example 2-1. A reduction rate of Co of the resultant catalyst and a percentage of a cubic phase in the crystal phase of Co metal are shown in Table 2-1.

(3) Production of Alcohol

An alcohol was produced by the same method as (3) in Example 2-1 using the resultant catalyst. A composition of the product was similarly determined. The composition of produced alcohol and residual fatty acid after the reaction is shown in Table 2-1.

Comparative Example 2-1

(1) Preparation of a Catalyst Precursor

A Co—Y—Pd oxide was prepared by the same method as (1) in Example 2-1.

(2) Activation of a Catalyst

The baked catalyst (oxide) and lauryl alcohol were charged in a 500 ml autoclave. The inside of the autoclave was substituted with hydrogen and raised to 5 MPa. The mixture was treated for 30 minutes at 250° C. The autoclave was cooled and the pressure was released. The reaction mixture was filtered to give a catalyst cake. For the catalyst cake, a percentage of a cubic phase in the crystal phase of Co metal is shown in Table 2-1.

(3) Production of Alcohol

An alcohol was produced by the same method as (3) in Example 2-1 using the resultant catalyst. A composition of the product was similarly determined. The composition of produced alcohol and residual fatty acid after the reaction is shown in Table 2-1.

drate in such amount as that an atom ratio of cobalt to molybdenum was 100:1, stirred and mixed in room temperature, and evaporated to dryness, and baked for 4 hours at 600° C. to give a Co—Y—Pd—Mo oxide. In the resultant baked catalyst, an atom ratio was Co/Y/Pd/Mo=100/2.5/0.07/1.1.

(2) Activation of a Catalyst

Figures 1, 3:
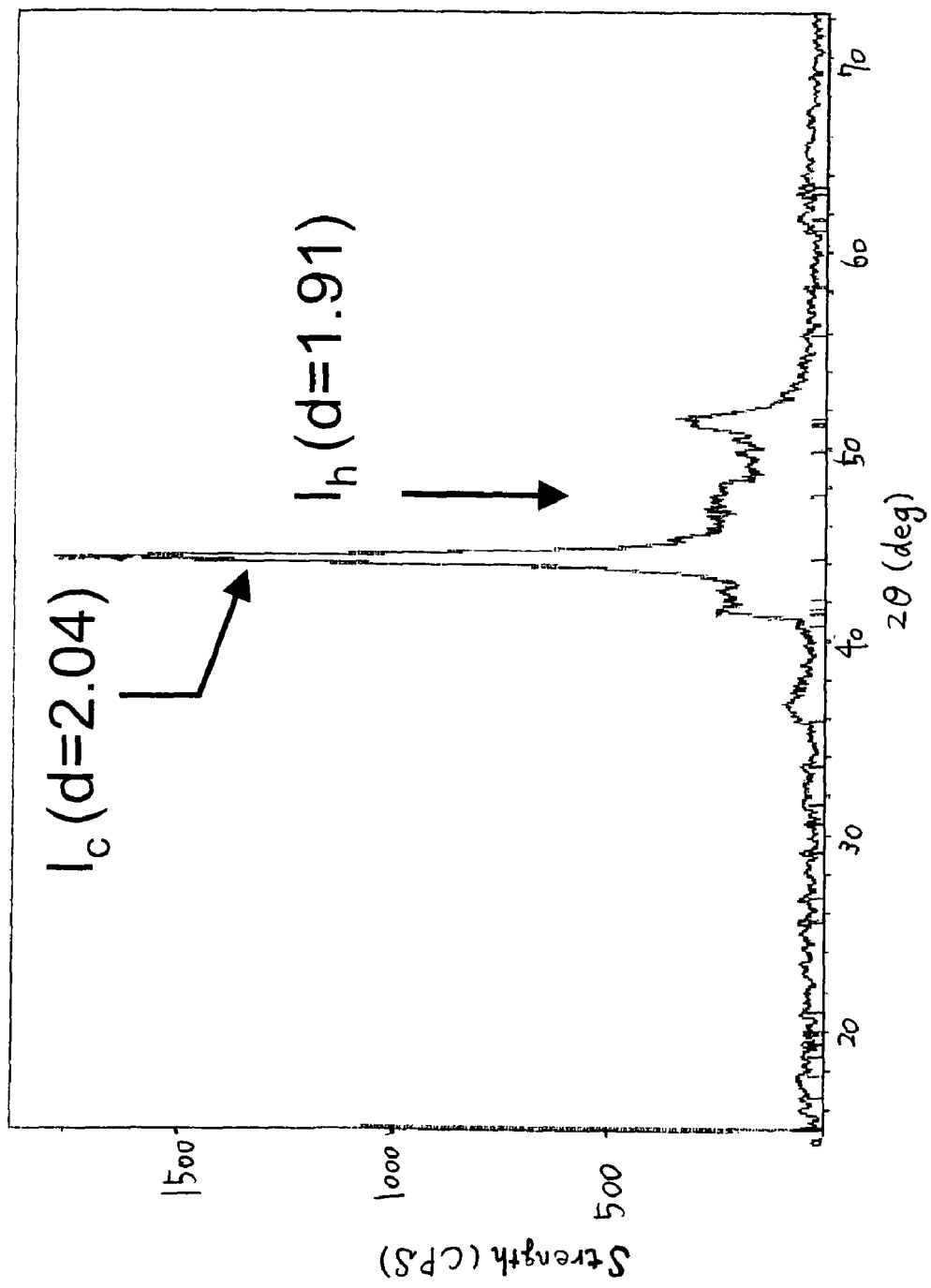

The baked catalyst (oxide) placed on a sintering dish was set in an electric furnace the inside thereof can be made to a reducing atmosphere. The furnace was flowed with 4% [v/v] of hydrogen diluted with nitrogen and raised to 500° C. The catalyst was subjected to a reduction treatment until hydrogen absorption was not detected. A reduction treatment time was 5 hours. The inside of the system was replaced with nitrogen and cooled to room temperature. Then, the furnace was flowed with the air diluted with nitrogen (oxygen concentration: 1% v/v) to oxidize and stabilize the surface of a reduced catalyst. The catalyst was subjected to the oxidation and stabilization treatment until oxygen absorption was not detected. The resultant catalyst was measured to calculate a reduction rate of Co from a real weight loss using a theoretical weight loss from Co oxide ($Co_3O_4$) to Co metal in the catalyst as 100. The catalyst was subjected to XRD analysis to give a peak pattern shown in FIG. 3-1. From the peak pattern, a percentage of a cubic phase in the crystal phase of Co metal was determined. Results are shown in table 3-1.

(3) Production of Alcohol 3.75 g (weight based on oxide) of the resultant catalyst and 150 g of lauric acid were charged in a 500 ml autoclave. The inside of the autoclave was substituted with hydrogen. The reaction was conducted for 40 minutes under conditions of 230° C./24.5 MPa/900 rpm/hydrogen 5 L/min flow. After the end of reaction, the autoclave was cooled and the pressure was released. The reaction mixture was filtered to collect a product (a first reaction). A composition of the product was determined by gas chromatography (GC) analysis as follows. The used catalyst was repeatedly used for production of alco-

TABLE 2-1

| | Kind of catalyst | Temperature of reducing catalyst (° C.) | Atmosphere for reducing catalyst | Reduction rate of Co (%) | percentage of Cubic phase in the crystal phase of Co metal (%) | Amount of used catalyst (%)[*1] | Composition of reaction product after 40 minutes reaction | |
|---|---|---|---|---|---|---|---|---|
| | | | | | | | Produced alcohol (%) | Residual fatty acid (%) |
| Example 2-1 | Co—Y—Pd | 500 | Gas phase | 85 | 100 | 2.5 | 56.7 | 1.00 |
| Example 2-2 | Co—Zr—Pd | 500 | Gas phase | 90 | 78.6 | 2.5 | 36.5 | 8.60 |
| Comparative example 2-1 | Co—Y—Pd | 250 | Liquid phase | 0 | 0[*2] | 2.5 | 14.4 | 27.0 |

[*1]weight of catalyst converted to oxide, relative to fatty acid raw material
[*2]In XRD analysis of activated catalyst, a crystal phase of Co metal was not detected and showed as "0%" for convenience of indication.

The aspect (2) will be described with reference to Examples below.

Example 3-1

(1) Preparation of a Catalyst Precursor

An aqueous solution of cobalt nitrate, yttrium nitrate (n-hydrate), and palladium nitrate mixed at 100:5:0.08 atom ratio of cobalt to yttrium to palladium and an aqueous ammonium carbonate solution were mixed and stirred at room temperature to produce a precipitate. The precipitate was sufficiently washed with water and dried at 110° C. To this was added an aqueous solution of hexaammonium heptamolybdate tetrahyhol by the same method. Compositions of produced alcohol and residual fatty acid in products of the first and a third reactions are shown in Table 3-1. Durability of the catalyst was evaluated according to the following method. A result thereof is also shown in Table 3-1.

<Method for Evaluating Durability of Catalyst>

A catalytic activity retention rate was determined from decreasing rates of acid value in the first reaction R1 (1/h) and in the third reaction R3 (1/h) according to the following calculation formula.

catalytic activity retention rate (%)=R3/R1×100

Example 3-2

(1) Preparation of a Catalyst Precursor

A Co—La—Pd—Mo oxide was prepared by the same method as (1) in Example 3-1, except that an aqueous solution of cobalt nitrate, lanthanum nitrate (hexahydrate) and palladium nitrate mixed at 100:5:0.08 atom ratio of cobalt to lanthanum to palladium was used. In the resultant baked catalyst, an atom ratio was Co/La/Pd/Mo=100/5.4/0.08/1.4.

(2) Activation of a Catalyst

The baked catalyst (oxide) was reduced, oxidized and stabilized by the same method as (2) in Example 3-1. A reduction rate of Co of the resultant catalyst and a percentage of a cubic phase in the crystal phase of Co metal are shown in Table 1-1.

(3) Production of Alcohol

An alcohol was produced by the same method as (3) in Example 3-1 using the resultant catalyst. Table 3-1 shows compositions of produced alcohol and residual fatty acid in reaction products of a first and a third reactions and a result of evaluation for durability of the catalyst.

Comparative Example 3-1

(1) Preparation of a Catalyst Precursor

An aqueous solution of cobalt nitrate, yttrium nitrate (n-hydrate), and palladium nitrate mixed at 100:5:0.08 atom ratio of cobalt to yttrium to palladium and an aqueous ammonium carbonate solution were mixed and stirred at room temperature to produce a precipitate. The precipitate was sufficiently washed with water, dried at 110° C., and baked for 4 hours at 600° C. to give a Co—Y—Pd oxide. In the resultant baked catalyst, an atom ratio was Co/Y/Pd=100/4.2/0.08.

(2) Activation of a Catalyst

The baked catalyst (oxide) was reduced, oxidized and stabilized by the same method as (2) in Example 3-1. A reduction rate of Co of the resultant catalyst and a percentage of a cubic phase in the crystal phase of Co metal are shown in Table 3-1.

(3) Production of Alcohol

An alcohol was produced by the same method as (3) in Example 3-1 using the resultant catalyst. Table 3-1 shows compositions of produced alcohol and residual fatty acid in reaction products of a first and a third reactions and results of evaluation for durability of the catalyst.

Examples 3 to 5

(1) Preparation of a Catalyst Precursor

A Co—Y—Pd—Mo oxide was prepared by the same method as (1) in Example 3-1. The resultant baked catalyst was supported on a carrier and formed.

To form a catalyst, $ZrO_2$ (Daiichi Kigenso Kagaku Kogyo Co., Ltd.; RC-100) as a carrier and $ZrO_2$ sol (Daiichi Kigenso Kagaku Kogyo Co., Ltd.; purity 30.5%) as a binder were used.

30% by weight of the baked catalyst and 70% by weight of the carrier $ZrO_2$ (RC-100) were mixed. To this was added 9% by weight of the binder $ZrO_2$ sol, and kneaded. The kneaded mixture was formed by extrusion molding with a vertical hydraulic extruder (cylinder volume: 100 cc) (inner diameter of dice: 2.5 mm).

The molded mixture was dried (120° C./15 hours) and baked (400° C./2 hours) to give a molded catalyst precursor. In the resultant molded catalyst, each of catalyst components/$ZrO_2$ carrier was 22%/78% (weight ratio), and an atom ratio of the catalyst components was Co/Y/Pd/Mo=100/6.0/0.07/1.7.

(2) Activation of a Catalyst

The baked catalyst (oxide) was reduced, oxidized and stabilized by the same method as (2) in Example 3-1. A reduction rate of Co of the resultant catalyst and a percentage of a cubic phase in the crystal phase of Co metal are shown in Table 3-2.

(3) Production of Alcohol

The resultant catalyst prepared in (2) was filled in a fixed-bed reactor, and used to hydrogenate lauric acid to produce a corresponding alcohol under conditions of temperatures, pressures and LHSV shown in Table 3-2. Compositions of produced alcohol and residual fatty acid under respective conditions are shown in Table 3-2.

TABLE 3-1

| | Kind of catalyst | Reduction rate of Co (%) | percentage of a cubic phase in the crystal phase of Co metal (%) | Amount of used catalyst (%)*[1] | Composition of reaction product | | | | Result of evaluation for durability of catalyst | | |
|---|---|---|---|---|---|---|---|---|---|---|---|
| | | | | | First time | | Third time | | Decreasing rate of acid value (1/h) | | Activity retention rate (%) |
| | | | | | Produced alcohol (%) | Residual fatty acid (%) | Produced alcohol (%) | Residual fatty acid (%) | First time | Third time | |
| Example 3-1 | Co—Y—Pd—Mo | 85 | 87 | 2.5 | 52.5 | 0.43 | 44.3 | 1.15 | 9.79 | 8.06 | 82 |
| Example 3-2 | Co—La—Pd—Mo | 100 | 85 | 2.5 | 28.7 | 16.1 | 23.4 | 16.7 | 5.79 | 5.51 | 95 |
| Comparative example 3-1 | Co—Y—Pd | 85 | 100 | 2.5 | 56.7 | 1.00 | 22.6 | 17.5 | 10.65 | 5.50 | 52 |

*[1]weight of catalyst converted to oxide, relative to fatty acid raw material

TABLE 3-2

| Kind of catalyst | | Reduction rate of Co (%) | Content of a cubic phase in the crystal phase of Co metal (%) | Temperature (° C.) | Pressure (MPa) | LHSV (1/h) | Composition of a sample taken at an outlet of a fixed-bed reactor produced alcohol | |
|---|---|---|---|---|---|---|---|---|
| | | | | | | | Produced alohol (%) | Residual fatty acid (%) |
| Example 3-3 | Molded Co—Y—Pd—Mo catalyst supported on ZrO$_2$ | 95 | 84 | 200 | 20 | 0.5 | 88.1 | 2.1 |
| Example 3-4 | | | | 200 | 9.8 | 0.5 | 83.2 | 2.8 |
| Example 3-5 | | | | 200 | 4.9 | 0.5 | 75.7 | 3.74 |

The invention claimed is:

1. A catalyst for producing an alcohol from a carboxylic acid by hydrogenation, comprising Co metal as an essential component and one or more elements selected from the group consisting of Zr, Y, La, Ce, Si, Al, Sc, V and Mo as a first co-catalyst component, and having 20% or more of cubic phase in the crystal phase of the Co metal,
wherein a reduction rate of Co in the catalyst is not less than 40%.

2. The catalyst for producing an alcohol according to claim 1, wherein the first co-catalyst component comprises one or more elements selected from the group consisting of Zr, Y, La, Ce, Si, Al, Sc and V.

3. The catalyst for producing an alcohol according to claim 1, further comprising one or more elements selected from the group consisting of Pt and Pd as a second catalyst.

4. The catalyst for producing an alcohol according to claim 3, comprising elemental Mo and a first co-catalyst other than the elemental Mo.

5. A method for producing a catalyst for producing an alcohol having 20% or more of cubic phase in the crystal phase of the Co metal, comprising:
reducing a catalyst precursor comprising Co and one or more elements selected from the group consisting of Zr, Y, La, Ce, Si, Al, Sc, V and Mo at a temperature of 300 to 800° C. under hydrogen atmosphere,
wherein a reduction rate of Co in the catalyst is not less than 40%.

6. The method for producing a catalyst according to claim 5, wherein the catalyst precursor comprises Co and one or more elements selected from the group consisting of Zr, Y, La, Ce, Si, Al, Sc and V.

7. The method for producing a catalyst according to claim 5, wherein the catalyst precursor further comprises one or more elements selected from the group consisting of Pt and Pd.

8. The method for producing a catalyst according to claim 7, wherein the catalyst precursor comprises elemental Mo and one or more elements selected from the group consisting of Zr, Y, La, Ce, Si, Al, Sc and V.

9. The method for producing a catalyst according to claim 5, further comprising forming an oxide film on the surface of a reduced catalyst to stabilize the catalyst after reducing the catalyst.

10. A method for producing an alcohol from a carboxylic acid as a raw material, comprising hydrogenating a carboxylic acid in the presence of the catalyst according to claim 1.

11. A method for producing the catalyst according to claim 1, comprising:
reducing a catalyst precursor comprising Co and at least one element selected from the group consisting of Zr, Y, La, Ce, Si, Al, Sc, V and Mo at a temperature of from 300 to 800° C. in the presence of hydrogen.

12. The method for producing a catalyst according to claim 6, further comprising forming an oxide film on the surface of a reduced catalyst to stabilize the catalyst after reducing the catalyst.

13. The method for producing a catalyst according to claim 7, further comprising forming an oxide film on the surface of a reduced catalyst to stabilize the catalyst after reducing the catalyst.

14. The method for producing a catalyst according to claim 8, further comprising forming an oxide film on the surface of a reduced catalyst to stabilize the catalyst after reducing the catalyst.

15. A method for producing an alcohol from a carboxylic acid as a raw material, comprising hydrogenating a carboxylic acid in the presence of the catalyst according to claim 2.

16. A method for producing an alcohol from a carboxylic acid as a raw material, comprising hydrogenating a carboxylic acid in the presence of the catalyst according to claim 3.

17. The catalyst for producing an alcohol according to claim 1, wherein said first co-catalyst component is present in an amount of 0.1 to 9.6 moles based on 100 moles of cobalt.

* * * * *